United States Patent [19]
Brenner et al.

[11] Patent Number: 5,968,540
[45] Date of Patent: Oct. 19, 1999

[54] METHOD FOR CONTROLLING A TARGET INSECT AND HYDRODYNAMIC INSECT BAIT

[75] Inventors: Richard J. Brenner, Gainsesville, Fla.; Kevin Burns, Carmel, Ind.

[73] Assignee: The United States of America, as represented by the Secretary of Agriculture, Washington, D.C.

[21] Appl. No.: 08/886,160

[22] Filed: Jun. 30, 1997

[51] Int. Cl.[6] .................................................. A01N 25/00
[52] U.S. Cl. ........................ 424/405; 424/84; 424/409; 424/410; 514/774; 514/778; 514/950
[58] Field of Search ................................ 426/1; 424/405, 424/409, 410, 84; 514/774, 778, 950

[56] References Cited

U.S. PATENT DOCUMENTS

| | | | |
|---|---|---|---|
| 3,755,064 | 8/1973 | Maierson | 161/174 |
| 4,211,668 | 7/1980 | Tate | 252/316 |
| 4,332,792 | 6/1982 | Kohn et al. | 424/84 |
| 4,439,488 | 3/1984 | Trimnell et al. | 428/402.24 |
| 4,563,836 | 1/1986 | Woodruff et al. | 43/131 |
| 4,774,081 | 9/1988 | Flashinski et al. | 424/78 |
| 4,774,082 | 9/1988 | Flashinski et al. | 424/78 |
| 4,823,506 | 4/1989 | Demarest et al. | 43/131 |
| 4,841,669 | 6/1989 | Demarest et al. | 43/131 |
| 4,845,103 | 7/1989 | Spaulding | 514/275 |
| 4,851,438 | 7/1989 | Flashinski | 514/531 |
| 4,889,710 | 12/1989 | Hagarty | 424/45 |
| 4,911,907 | 3/1990 | Shimamura et al. | 424/84 |
| 4,923,897 | 5/1990 | Flashinski | 514/531 |
| 4,945,107 | 7/1990 | Minetti | 514/473 |
| 4,988,510 | 1/1991 | Brenner et al. | 424/84 |
| 4,990,514 | 2/1991 | Bruey | 514/275 |
| 5,021,237 | 6/1991 | Bruey | 514/275 |
| 5,052,618 | 10/1991 | Carlon et al. | 239/77 |
| 5,126,139 | 6/1992 | Geary | 424/410 |
| 5,192,671 | 3/1993 | Arison et al. | 435/101 |

FOREIGN PATENT DOCUMENTS

| | | |
|---|---|---|
| 7376687 | 3/1987 | Australia . |
| 0254257 | 7/1987 | European Pat. Off. . |

OTHER PUBLICATIONS

Advertising Brochure, "Tree Guard", Unknow.
Peeters, G. J., "Compositions for Combating Cockroaches", Chem. Abstract 84:131508d, vol. 84, p. 151, 1976.
Doi et al., "Baits for cockroach control", Chem. Abstract 107:129156n, vol. 107, p. 265, 1987.
Jackson et al., "Dispersion of Marked American Cockroaches From Sewer Manholes in Phoenix, Arizona", Am. J. Trop. Med Hyg., vol. 4, pp. 141–146, 1955.
Appel, et al., "Outdoor Activity and Distribution of the Smokybrown Cockroach, *Periplaneta fuliginosa* (Dictyoptera: Blattidae)", Env. Ent., vol. 14, No. 6, pp. 660–673, 1985.
Reierson et al., "Trapping, Flushing, Counting German Roaches", Pest Control, pp. 40–44, Oct. 1977.
Brenner, R. J., "Focality and Mobility of Some Peridomestic Cockroaches in Florida (Dyctyoptera: Blattaria)", Annals of the Ent. Soc. of America, vol. 81, No. 4, pp. 581–592, 1988.
Brenner et al., "Laboratory Feeding Activity and Bait Preferences of Four Species of Cockroaches (Orthoptera: Blattaria)", J. Econ. Ent., vol. 82, No. 1, pp. 159–162, 1989.
Adler, V. E., "A Highly Effective Attractant for the Brown-banned Cochroach (Opthptera: Blattellidae)", J. Environ. Sci. Health, vol. A20, No. 8, pp. 839–844, 1985.
Jackson et al., "Additional Studies of Dispersion Patterns of American Cockroaches From Sewer Manholes in Phoenix, Arizona", The Ohio, J. or Sci, vol. 6, No. 4, pp. 220–226, Jul. 1961.

*Primary Examiner*—Milton Cano
*Attorney, Agent, or Firm*—M. Howard Silverstein; John D. Fado; Gail E. Poulos

[57] ABSTRACT

Hydrodynamic baits for the control of orthopterous insects are disclosed which contain an attractant, a humectant and a gel former. The baits are designed to function in harsh and/or dynamic microclimates such as for example commercial kitchens or outdoor environments subject to typical circadian influences such as temperature and moisture. A further advantage of the disclosed baits is their lack of attractiveness to mammals.

19 Claims, 9 Drawing Sheets

METHOD FOR CONTROLLING A TARGET INSECT AND HYDRODYNAMIC INSECT BAIT

BACKGROUND OF THE INVENTION

1. Field of the Invention

This invention relates to a system for the control of insects, especially cockroaches, that includes hydrodynamic baits, that can be flowable or formable, and to a method for controlling insects, especially cockroaches, using the hydrodynamic baits.

2. Description of the Related Art

Cockroaches are primarily tropical insects but some species have become widely disseminated through commercial activities and are now cosmopolitan. The domestic species are omnivorous but are especially attracted to starchy or sweetened matter of various kinds; they also attack food, paper, clothing, books, shoes, bones, and dead insects. They are the orthopterous insects that are involved in the contamination of food. Of the many species of cockroaches, house inhabitors include American (*Periplaneta americana*), oriental (*Blatta orientalis*), Australian (*P. australasiae*), German (*Blattella germanica*), brownbanded (*Supella longipalpa* (F.)), smokybrown (*P. fuliginosa* (Serville)), and Florida woods (*Eurycotis floridana* (Walker)) cockroaches. They prefer secluded, warm, damp places and at night or on dark days, they sample filth and foods and impart to infested areas an unpleasant odor.

A number of food attractants have been formulated with toxicants and aqueous gel binders to provide toxic paste baits for cockroaches. For example, Doi et al. (Chem. Abst. 107:12915n(1987)) controlled cockroaches with a paste containing boric acid, potato strach, corn strach, rice bran, molasses, water, and dye; Barson (Chem. Abst. 97:87017k (1982)) used a mixture of boric acid plus porridge oats and iodofenphos gel; Peeters (Chem. Abst. 84:131508d (1976)) combined bakery wastes, boric acid, and water. Similarly, the proprietary roach bait station sold under the trademark, "It Works" (Bridgeport, Conn.) is advertised as containing boric acid, an attractant, and a humectant.

One of the key necessities for arthropod survival is moisture. When temperatures increase, the metabolism of cockroaches and other insects increase. Subsequently, they have an increased need for food and will find a bait that is also a good moisture source. Silverman (Australian Document No. AU-B-73766/87) discloses a bait that incorporates water as an attractant to lure cockroaches to a poisoned bait. The bait is a solid, non-particulate, non-flowable, non-repellent, fully edible insecticide-bait composition with a pentadienone hydrazone insecticide compound, a specific food attractant system and a binder. The water attractant can be in a container close to the bait or in a cup-like container built into the feeding station containing the bait. The water can also be formulated into the bait using a water absorbent material such as a water absorbing polymer, especially an electrolyte polymer that does not contain natural polymer such as starch and contains synthetic carboxylate and hydroxyl groups, has a high water-absorption ratio and has excellent water-retaining properties as well as good strength after absorbing water. The particular polymers are a saponified copolymer of vinyl ester (x) and ethylenic unsaturated carboxylic acid or its derivative (y) sold under the name SUMIKAGEL® S-50 and the polyvinyl alcohol-acrylate graft polymer.

Ong (U.S. Pat. No. 4,812,309) discloses a gel composition for the control of cockroaches that includes a gellant, propyl p-hydroxybenzoate, propylene glycol, fatty acids, an insecticide, high fructose corn syrup, isopropyl alcohol, methyl p-hydroxybenzoate and water where the gellant is a non-ionic surfactant. The composition can be distributed so that it poses little or no hazard to humans or animals that may frequent the infested area.

Brenner et al (U.S. Pat. No. 4,988,510, herein incorporated by reference) disclose a hydrophilic gel bait which is deformable (non-flowable) that includes corn distiller's grains with solubles as an attractant for cockroaches. This bait includes a humectant, insecticide, a gel former, and optionally a preservative. This bait provides both food and a relatively moist environment for cockroaches.

Dried mash from a distillery was reported by Adler (J. Environ. Sci. Hlth., A20:839–844(1985)) to be specifically attractive for the brownbanded cockroach, *Supella longipalpa* (F.), but it failed to attract American cockroaches, *Periplaneta americana* (L.). In contrast, Brenner et al (Ann. Entomol. Soc. Am. 81:581–592 (1988); J. Econ. Entomol. 82:159–162(1989)) reported that distiller's dried grains with solubles (DDGS, Agricultural Energy Corp., Franklin, Ky.) was attractive to 15 species of cockroaches including American cockroaches. Furthermore, the DDGS is advantageously unattractive to nontarget mammals, in contrast to other baits such as pieces of fruit, bread, and beer (Jackson et al., Am. J. Trop. Med. Hyg. 4:141–146 (1955); Ohio J. Sci., 61:220–226 (1961); Reierson et al., Pest Control 45:40, 42–44 (1977); Fleet et al., Environ. Entomol. 14:669–673 (1985) or dry cat food (Appel et al., Environ. Entomol. 14669–673(1985)) which are attractive to mammals as well as cockroaches.

Bruey (U.S. Pat. No. 5,021,237) discloses a gel insecticide bait that is dispensed from a pressurized container which is made up of a pentadienone hydrazone as a toxicant, a fatty acid, a lower alcohol, a sugar, a gellant, water, a base and a hydrocarbon propellant. The gel bait composition is an oil-in-water emulsion of a toxicant-fatty acid mixture in a corn syrup solution. It is sufficiently fluent to be dispensed from a pressurized package and the deposited form will retain sufficient bulk to be ingested by cockroaches over a long period of time.

While various gel baits have been developed for the control of insects, especially cockroaches, there still remains a need in the art for a more effective bait form that provides food and moisture, especially when insects are most in need of food and moisture. The present invention provides hydrodynamic insect baits which function well in harsh microclimates and are different from the prior art baits and solves some of the problems associated with prior art baits.

SUMMARY OF THE INVENTION

It is therefore an object of the present invention to provide an insect bait which is hydrodynamic and functions under harsh and/or dynamic microclimates such as for example household or commercial kitchens, attics, sewers, etc..

Another object of the present invention is to provide an insect bait which continually charges and discharges moisture.

A still further object of the present invention is to provide an insect bait that is strongly attractive to well-fed insects and does not attract mammals.

It is also an object of the present specification to provide an insect bait that is widely attractive to various species of the target insect.

Another object of the present invention is to provide a flowable bait which continually charges and discharges moisture.

Another object of the present invention is to provide an insect bait containing about 5–90% of an attractant, about 5–60% of a humectant and about 1–30% of a gel former.

A still further object of the present invention is to provide an insect bait that contains pregelatinized starch as a component of the bait.

A further object of the present invention is to provide a bait that contains glycerin and fructose syrup as the humectant component of the bait.

Further objects and advantages of the present invention will become apparent from the following description.

DETAILED DESCRIPTION OF THE INVENTION

The baits of the present invention are particularly useful for controlling typical orthopterous insects principally cockroaches. Without limitation thereto, exemplary cockroaches include *Blattella germanica* (L.), *Blattella asahinai* Mizukubo, *Supella longipalpa* (F.) *Cariblatta lutea* lutea (Saussure and Zehntner), *Eurycotis floridana* (Walker), *Ischnoptera deropeltiformis* (Brunner), *Latiblattella rehni* Hebard, *Panchlora nivea* (L.), *Parcoblatta caudelli* Hebard, *Parcoblatta divisa* (Saussure and Zehntner), *Parcoblatta fulvescens* (Saussure and Zehntner), *Parcoblatta lata* (Brunner), *Blatta orientalis* L., *Periplaneta americana* (L.), *Periplaneta fuliginosa* (Serville), *Periplaneta australasiae* (Fab.), *Periplaneta brunnea* Burmeister and *Pycnoscelus surinamensis* (L.). The baits of the present invention are hydrodynamic and function well in harsh microclimates or dynamic microclimates, such as an outdoor environment subject to typical circadian influences of temperature and moisture. Under conditions of high moisture content in the air, the baits absorb water, then release it under more xeric conditions. Consequently, the baits continually charge and discharge moisture, which is one of the key components for arthropod survival. This release of moisture commonly occurs as temperatures rise with a concomitant drop in humidity. Higher temperatures increase the metabolism of cockroaches and other insects. Subsequently, they have an increased need for food and find a bait that is also a good moisture provider. The baits of the present invention are developed against highly preferable food substrates so that it is strongly attractive to well-fed insects. They contain several food components, that when combined, provide unexpected results in attractiveness and hydrodynamics. One formulation is flowable and can be delivered from a syringe- or tube- configuration and use of small-aperture adapters allows the bait to be placed strategically in inaccessible areas, providing a high safety factor. Any toxic material can be used as the active ingredient. The toxicant can also be omitted and a non-toxic version can be used as an attractant for any sticky trap or live trap device. Also, because the matrix is so hydrodynamic, it can be used as a substrate for biological control agents that commonly have high moisture requirements such as, for example, nematodes. The formable bait can be placed in any type of known bait station. It can also be applied to a rough surface, such as for example any type of mesh screening, such as for example wire, vinyl, fiberglass, aluminum, etc.; and applied to any surface.

The baits contain a grain component, such as for example, corn distillers grain with solubles, that is high in protein and contains volatile food attractants. To further increase the hydrodynamic character of the baits, high fructose corn syrup and glycerin are included with pregelatinized starches in the bait formulation. The use of a pregelatinized starch in the presence of glycerin forms a glycerostarch complex that greatly maintains pliability and adhesiveness of the material over time. This results in a bait that can be used under broad environmental conditions that include horizontal and vertical surfaces under changeable microclimates such as, for example, commercial kitchens characterized by stainless steel surfaces with high ambient temperatures and humidities. Optional ingredients include a preservative to retard fungal growth, peanut butter to augment attractiveness and a protectant such as a bittering agent to provide a safety factor for exposed bait.

The attractant is defined as any substance or combination of substances which will lure orthopterous insects, especially a broad spectrum of cockroach species and other insects. The attractants include, for example, corn distiller's dried grains with solubles, herein after referred to as C-DDGS, peanut butter, etc. and combinations thereof. U.S. Pat. No. 4,988,510 (Brenner et al), herein incorporated by reference in its entirety, discloses that corn distiller's dried grains (C-DDGS) with solubles obtained from nonbeverage alcohol production, is highly effective as a bait for most species of peridomestic cockroaches but is not attractive to mammals such as dogs, cats, raccoons, and wood rats. The most preferred C-DDGS, for the purposes of this disclosure, is grain H (Distiller's dried grains-solubles) from Midwest Grain Products of Illinois (P.O. Box 1069, Pekin, Ill. 61555-1069) which is strongly preferred by insects. Grain H includes a small quantity of wheat with the corn.

Humectants useful in the present invention include, for example, any hygroscopic substance or combination of substances that draw moisture from the air, allowing the bait formulation to remain relatively moist and pliable. Sugars such as for example high fructose corn syrup, polyhydroxy alcohols such as glycerin, combinations thereof, etc. are exemplary of the substances useful for this purpose. Some humectants, such as sugars, provide the further advantage of enhancing the attractiveness of the bait. A most preferred humectant is a combination of glycerin and corn syrup wherein the corn syrup is 95% fructose (Archer Daniels Midland corn syrup).

The toxicant can be any toxicant suitable for control of the particular insect, including biocontrol agents such as for example nematodes. Examples of chemical toxicants include organophosphates such as diazinon, malathion, chlorpyrifos, fenitrothion, prormiphos, fenthion, phoxim, acephate, methacrifos; carbamates such as, for example, baygon, propoxur, bendiocarb, dioxacarb,carbaryl; natural pyrethroid such as for example pyrethrin; and synthetic pyrethroids such as, for example, sumithrin, tetramethrin, d-trans allethrin, and s-bio allethrin and metabolic inhibitors such as for example hydramethylnon. The insecticide can be microencapsulated wherein the microcapsule is semipermeable in the absence of free water and impermeable in a wet environment. This prevents the loss of insecticide by leaching, but permits release when the capsules are physically crushed, as during the act of chewing by cockroaches. By using microencapsulated toxicants, the only substantial release of toxicant in the insect habitat is within the alimentary tracts of the target organisms. If the threat of leaching is not a factor or the toxicant is not repellent, it can be mixed directly into the bait composition.

Gel formers for use herein provide an elastic, cohesive matrix that holds the attractant together in combination with other bait ingredients. Any gelling agent that is not repulsive to insects can be used, provided that the resultant matrix freely releases the aromatic elements of the attractants. Examples of useful gelling agents include pregelatinized wheat starch, found to be superior to all other starches; pregelatinized tapioca, pregelatinized potato, and pregelatinized corn starch. Corn is also found to be an excellent starch for a food attractant. The starches useful in the invention include, for example, pregelatinized wheat starch such as for example PAYGEL™ (A. E. Staley Co., Decatur, Ill. 62525) pregelatinized tapioca, such as for example STA-SLIM 150™ (A. E. Staley) pregelatinized potato, such as for example STA-SLIM 142™ (A. E. Staley) pregelatinized corn starch such as for example MIRA-GEL® etc. These starches are used both for the flowable and the formable baits. The most preferred gelling agent is PAYGEL 290™ (Archer Daniels Midland. Keokuk, Id. 52632). When a formable bait is desired, a second gel former is added. This second gel former includes any animal gelatin such as, for example, pork, beef, horse, etc. Pork gel (SBI Sanofi Bio Industries, Inc., Debuque, Iowa) is most preferred.

Preservatives are optional in the baits of the invention but are recommended for baits used in very humid or moist conditions. Examples of preservatives useful in the present invention are 1,2-benzisothiazolin-3-one (PROXEL GXL™, ICI Americas, Wilmington, Del. 19897) methyl paraben (p-hydroxybenzoic acid methyl ester) and propyl paraben (n-propyl p-hydroxybenzoate). Other known fungistats would also be effective in increasing the longevity of the bait and retarding mold growth.

Each component should be present in an effective amount. The expression "effective amount" is defined herein to mean that amount which is necessary to achieve the intended result of the component in question. For, example, an effective amount of the toxicant is that level or concentration which will kill significantly more target insects when the bait is consumed than when an equivalent amount of bait is consumed without the insecticide present. Likewise, an effective amount of attractant is that which will attract more target insects to the bait than a control bait without the attractant. On a dry weight basis, the components of the bait composition will typically be present in about the following amounts: 5–90%, 10–60% preferred and 10–35% most preferred for the attractant; 0.1–20%, 5–60% preferred and 40–60% most preferred for the humectant; 1–30%, 1–20% preferred and 2–15% most preferred for the gel former; 0–50%, 0–10% preferred and 0–5% most preferred for the toxicant; and 0–5% preferred and 0–2% most preferred for the protectant. The most preferred dry weight concentrations are:

For a flowable bait: about 28.5% for the attractant, about 5.2% for the gel former, about 45.6% for the humectant, about 0.5% for the toxicant, about 0.2% for the preservative, about 1.2% of a bittering agent and about 18.8% water.

For a formable bait: about 32.2% for the attractant, about 9.6% for the gel former wherein about 4.8% is a pregelatinized starch and about 4.8% is an animal gel, about 43.0% for the humectant, about 0.5% for the toxicant and about 15.1% water.

To prepare both the flowable and formable bait formulations, a paddle-type mixer, such as a Hobart paddle mixer for example, is charged with the gel former and the attractant. A combination of the humectant and the toxicant are mixed and warmed to 50° C. and then sprayed into the ingredients in the mixer. Optional ingredients such as a preservative, an additional humectant such as fructose sugar, and a bittering agent, are added to the water. Water or water containing the optional ingredients are added to the mixer with agitation. If peanut butter is used, it is folded in last.

To apply the formulations of the present invention, the flowable bait can be dispensed from a syringe- or tube-configuration and the use of small-aperture adapters allows the bait to be placed strategically in inaccessible areas, providing a high safety factor. The formable bait can be rolled and cut into any shape and size. It can be placed in any type of bait station or applied to any type of adhering surface such as for example applying it to a mesh screen, VELCRO, etc., and attached to any surface.

The following examples are intended only to further illustrate the invention and are not intended to limit the scope of the invention which is defined by the claims.

EXAMPLE 1

PREPARATION OF THE FLOWABLE BAIT

A HOBART paddle mixer is charged with premilled Grain H (Midwest Grain Products of Illinois, Pekin, Ill.) and PAYGEL 290. A combination of glycerin and chlorpyrifos (toxicant) is warmed to about 50° C. and sprayed into the mixer onto the agitated mixture. A combination of PROXEL GXL, high fructose corn syrup (ADM CS95) and an aqueous solution of BITREX is added with agitation to form a gel paste. Finally, warmed peanut butter is folded into the paste to furnish the flowable bait.

PREPARATION OF FORMABLE BAIT

The formable bait is prepared as above for the flowable bait with the addition of granular pork gelatin to the paddle mixer along with the premilled grain H and PAYGEL.

EXAMPLE 2

Hydrodynamic studies were preformed to determine the moisture retention of the formable bait. The formable bait formulations are prepared using the following amounts:

PAYGEL Plus (PAYGEL+) formable bait contains about 24.3% grain H, about 4.8% pork gel, about 4.8% glycerin, about 14.1% water, about 47.3% high fructose corn syrup, about 4.8% PAYGEL and about 0.1% PROXEL.

PAYGEL formable bait contains about 27% grain H, about 4.8% PAYGEL, about 47.3 corn syrup containing fructose, about 4.8% pork gel and about 12.7% water.

The grain H is ground five times using a Straub Model 4E grinding mill. The grain H, pork gel and PAYGEL are combined and manually mixed well. The water and glycerin are combined and added to the high fructose containing corn syrup. This liquid composition is slowly added to the dry ingredients with continuous mixing at ambient conditions. For the purposes of this specification, ambient conditions are defined as laboratory air; approximately 40–50% relative humidity. Controls are FARLEY'S Grape Snack (FGS) (FARLEY Candy Company, Chicago, Ill.) and RAT CHOW. Approximately 0.75 grams of each bait was molded into tube shapes by extruding the preparation into a piece of tubing that is about 5.0 mm I.D. and about 2.0 cm in length. The unmolded bait is placed onto number 3 insect pins and placed into a container with a screened top. Bait weights were determined at ambient conditions once daily (approximately every 24 hours) thereafter for the duration of the study. The data were then analyzed in TableCurve (Jandel Scientific) establishing the equilibrium point where the baits no longer lost weight due to the loss of moisture.

Figure 1:
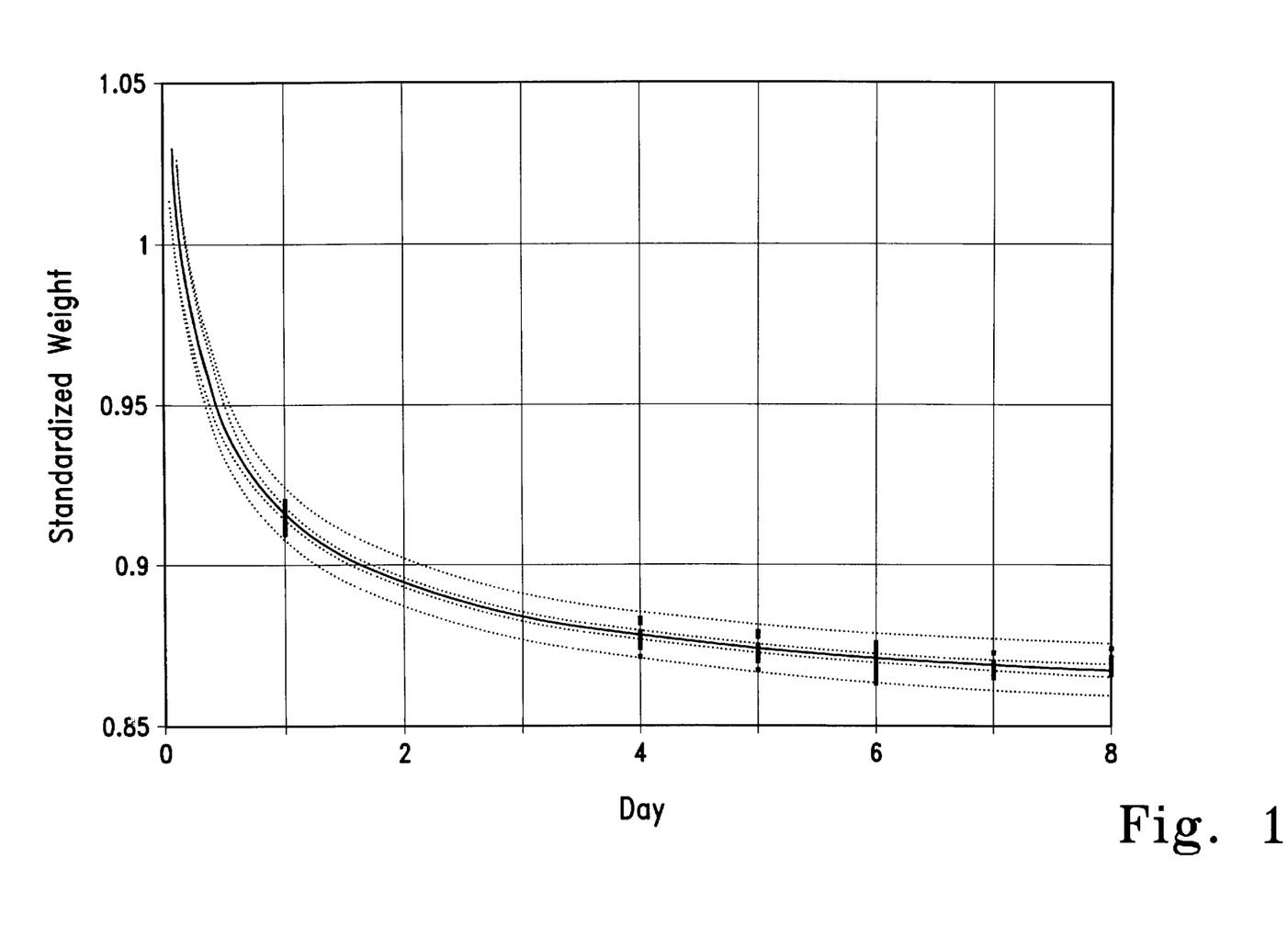
FIG. 1 is a graph showing the hydrodynamics of a formable gel, PAYGEL Bait, containing about 27% DDGS, about 4.8% pregelatinized wheat gel former, about 47.3% corn syrup containing fructose (humectant) and about 4.8% pork gel (gel former) and about 12.7% water.
Figure 2:
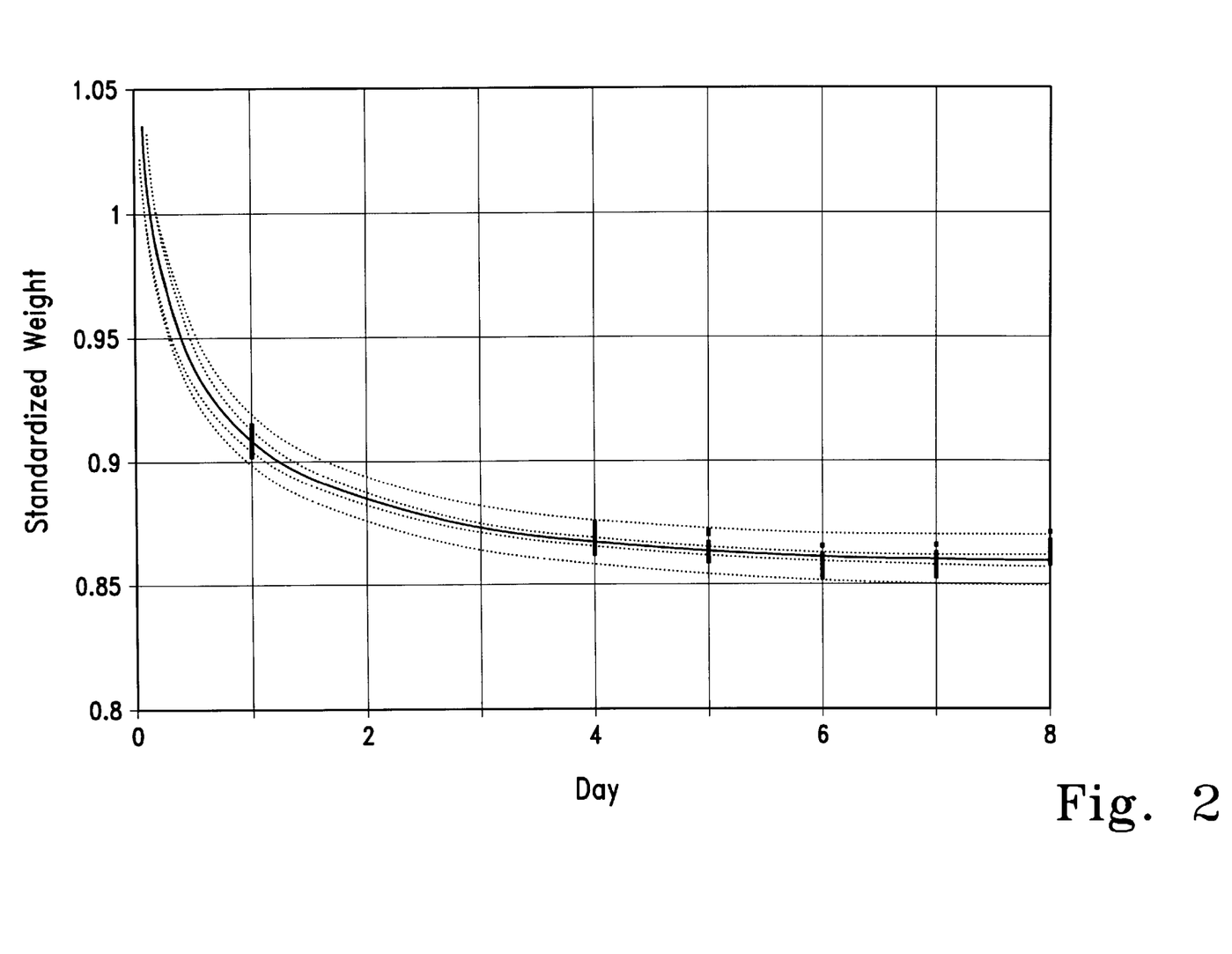
FIG. 2 is a graph showing the hydrodynamics of a formable gel bait, PAYGEL Plus, containing about 24.3% DDGS, about 4.8% pregelatinized wheat gel former, about 47.3% corn syrup containing fructose (humectant), about 4.8% glycerin (humectant), 4.8% pork gel, and about 14.1% water.

Comparisons were made using equation 6301 which is: $y=a+b\ln x+c(\ln x)^2+d(\ln x)^3$. The results are shown in FIGS. 1 and 2. In FIGS. 1 and 2, the $r^2$ values were $r^2=0.995909526$, DF Adj $r^2=0.995750673$, FitStdErr=0.00307213905 and Fstat=8440.3086; and $r^2=0.995540285$, DF Adj $r^2=0.995367093$, FitStdErr=0.00344699836 and Fstat=7738.62611; respectively. These results indicate that the formable bait without glycerin retains moisture slightly better than the formable bait containing about 10% less grain H and the addition of equal parts by weight of glycerin and water (formulation described above in Example 1). However, the addition of glycerin and water gives a consistency to the bait which is more stable over time allowing the formable bait to be rolled out even 1 week post formulation.

Furthermore, the addition of glycerin and water increases consumption of the bait slightly. All stages of cockroaches consume more of the bait containing glycerin except for males at day 2 (Table 1 below). Male, female and nymphs of German HRDC strain cockroaches were sorted into large battery jars with 3 reps of 100 cockroaches for each sex/stage. The cockroaches were then placed on a diet of FARLEY'S Grape Snacks (FGS), RAT CHOW and water for 48 hours prior to introduction of the baits of the present invention. Bait stations were made by passing a #3 insect pin of approximately 1 inch in length through about a 5 dram vial snap cap, with the snap cap functioning as a base for the bait station. The PAYGEL Plus and PAYGEL baits were formed by placing the bait into a cookie press and squeezing the bait into an approximately 0.75 inch of about 0.25 inch I.D. TYGON™ tubing. The bait and tube were slid onto the map pin and the bait was pushed out of the tubing with a nail head, sliding the tubing over the nail leaving the bait stuck on the pin. FARLEY'S Grape Snacks were also presented using the same style bait station by simply sliding the snacks onto the pins. As RAT CHOW tended to crumble when attempting to place it on the map pin, it was presented by placing a piece of the CHOW on a 5 dram snap cap lid. Once the experimental baits were formed, they were weighed on an OHAUS model #GA200D electronic balance and placed in a RUBBERMAID brand food container with a screen lid and allowed to age at ambient conditions for about 6 days before introduction. On about the 6th day of aging, 1 bait for each bait tested, was placed into each battery jar which already contained bait stations of FGS and RAT CHOW, placed 48 hours prior, and 1 control experimental bait was placed into a screened container (which also contained control FGS and rat chow) in the same battery jar. If the FGS bait station had been consumed by more than ½, they were replaced with new FGS stations. All experimental baits, FGS stations, rat chow stations and their corresponding control stations were weighed prior to placement in the battery jars and daily for the next two days to determine consumption. Consumption of each food source was measured by adjusting the daily weight change of the test bait (Ta) by the proportion weight change in the control (hereafter , "test bait" refers to any bait for consumption—e.g. RAT CHOW, FGS, PAYGEL bait or PAYGEL Plus bait) . Therefore, $Ta=(C_i/C_{i-1})(T_{i-1}-T_i)$, where $C_i$=current weight for control, $C_{i-1}$=previous day's weight for control, $T_{i-1}$=previous day's weight for test bait and $T_i$=current weight for test bait. The mean adjusted consumption was calculated for the 3 reps of each stage for each day of feeding and were analyzed by analysis of variance using the General Linear Model statement with the means separated by Tukey's studentized range test.

TABLE 1

Evaluation of Paygel Combo vs Paygel Plus baits. ENHANC31.XLS

| Day | Stage | Bait | Mean Consumption (mg) | Tukey's Grouping |
|---|---|---|---|---|
| 1 | Female | Paygel + | 212.97 | A |
| | | Paygel | 132.75 | A |
| | | FGS | 48.90 | B |
| | | RAT CHOW | 18.03 | B |
| | Male | Paygel + | 67.99 | A |
| | | FGS | 65.58 | A |
| | | Paygel | 37.07 | AB |
| | | RAT CHOW | 0.77 | B |
| | Nymph | Paygel + | 113.95 | A |
| | | Paygel | 83.49 | AB |
| | | RAT CHOW | 30.54 | B |
| | | FGS | 27.08 | B |
| 2 | Female | Paygel + | 73.16 | A |
| | | Paygel | 67.09 | AB |
| | | FGS | 44.60 | AB |
| | | RAT CHOW | 11.22 | B |
| | Male | FGS | 69.35 | A |
| | | Paygel + | 38.95 | B |
| | | Paygel | 16.02 | BC |
| | | RAT CHOW | −1.27 | C |
| | Nymph | Paygel + | 68.68 | A |
| | | Paygel | 52.97 | A |
| | | RAT CHOW | 40.01 | A |
| | | FGS | 25.63 | A |

EXAMPLE 3

The hydrodynamics of the baits of the present invention were evaluated along with COMBAT Superbait (2% Hydramethylnon), Raid Roach bait station (0.5% DURSBAN) and Max Force gel (2% Hydramethylnon). The baits are prepared as follows: COMBAT Superbaits and RAID Roach baits were removed from their containers and placed on standard bait pins (#3 insect pins pushed upwards through the center of a plastic cap taken from a 2-dram snap cap vial). The gel baits (DE Gel for the flowable bait of the present invention) were formed by squeezing a dime size drop of bait in the bottom of a souffle cup (about 29.5 ml) and placing the cup on bait pins. The formable bait of the present invention (DE station) was formed by rolling the bait onto wax paper and using a vial cap (screw type) to cut the baits out and then place them on the pins. DE station baits were approximate in size to the COMBAT and RAID station baits, except where cylinder shaped (See Example 2 for dimensions). The flowable and formable bait formulations used in this example are:

Formable bait: about 30.2% Grain H, about 5.5% PAYGEL 290™, about 5.5% pork gel, about 3.7% glycerin, about 15.1% water, about 0.2% PROXEL GXL, about 39.3% corn syrup containing fructose and about 0.5% chlorpyrifos.

Flowable bait: about 25.2% Grain H, about 5.5% PAYGEL 290™, about 8.7% glycerin, about 0.5% chlorpyrifos, about 0.2% PROXEL GXL, about 39.3% corn syrup containing fructose and about 20.6% water.

Figure 3:
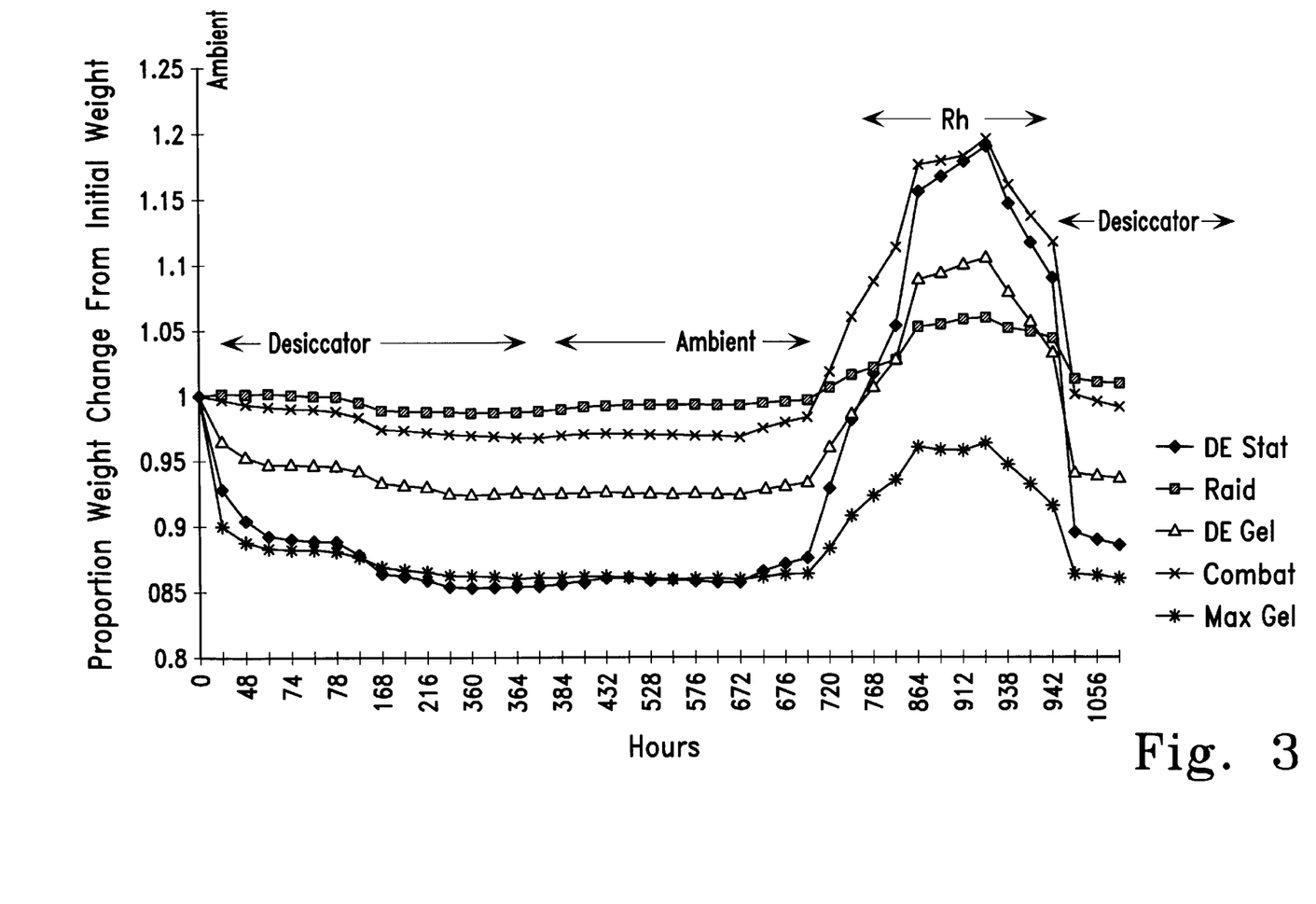
FIG. 3 is a graph comparing bait hydrodynamics of the flowable bait of the instant invention (DE Gel), formable bait of the instant invention (DE Stat), RAID™, COMBAT™ and SIEGE™ under dry (desiccator, about 15% relative humidity), followed by ambient (laboratory air; approximately 40–50% relative humidity), followed by humid (humidity chamber, approximately 100% relative humidity) and then finally dry again. The weights are under various conditions and are compared to the initial weights of the bait.
Figure 4:
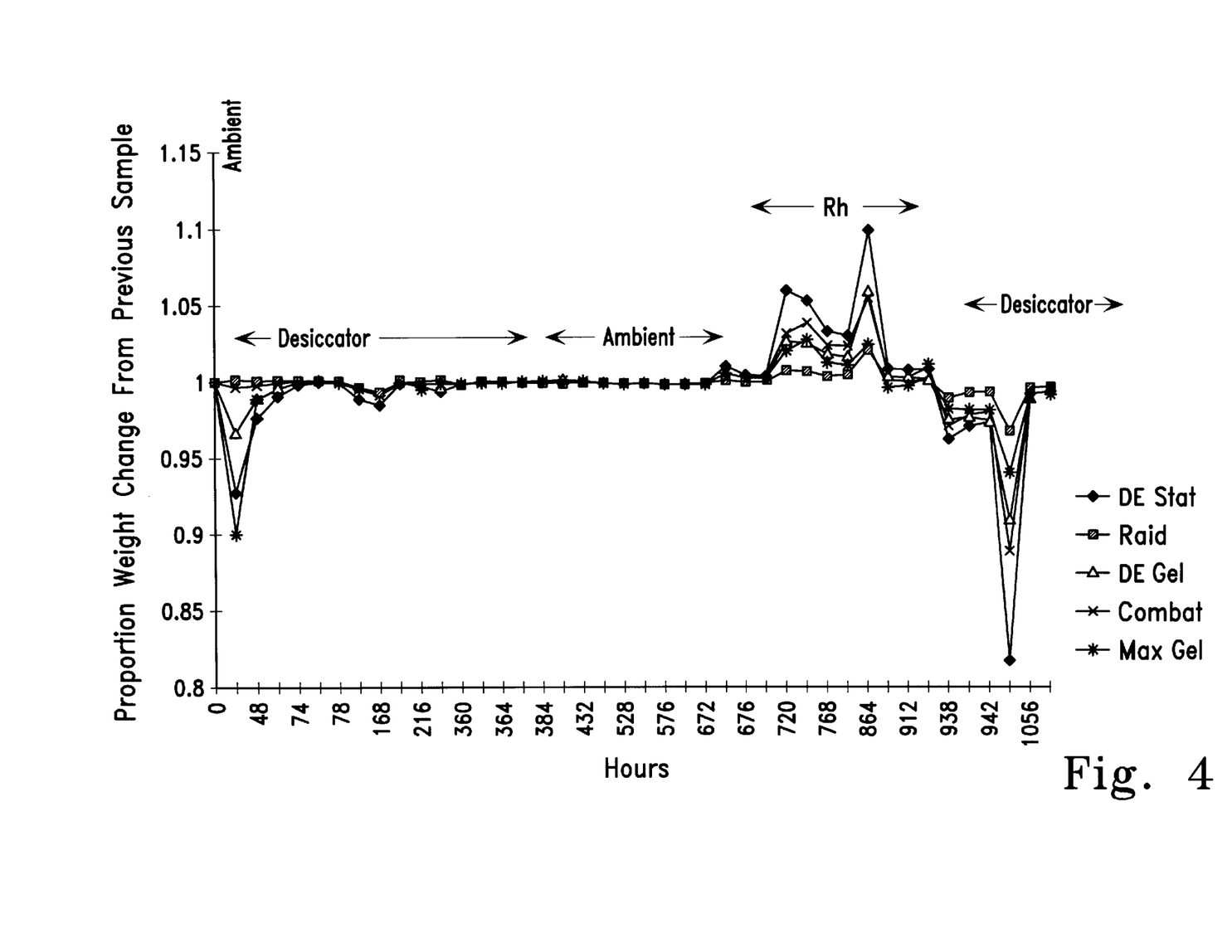
FIG. 4 is a graph comparing bait hydrodynamics of a flowable bait of the instant invention (DE Gel), a formable bait of the instant invention (DE Stat), RAID™, COMBAT™ and SIEGE™ under the same conditions as FIG. 3 above. The weights of the baits under the various conditions are compared to the previous weight of that bait.

Baits were weighed on an OHAUS electronic balance (model #GA200D) at ambient conditions and left at ambient conditions in a screen-top container (RUBBERMAID) for about 4 days. On about the 4th day baits were again weighed at ambient conditions and then placed in a desiccator. Baits were then removed from the desiccator at 2, 4 and 6 hours and weighed quickly at ambient conditions. Weights were then taken daily until the baits became stable. When stability was reached, the baits were removed from the desiccator and left at ambient conditions. Bait weights were taken at 2,4 and 6 hours and then daily until stable. When stability was reached, the baits were placed in a 100% relative humidity (RH) chamber (RUBBERMAID tub containing wet paper towels). The baits were weighed quickly under ambient conditions at 2, 4 and 6 hours and then daily until stability was reached. Once stability was reached, the baits were removed from the RH chamber and left at ambient conditions for a final time, again taking weights at 2,4 and 6 hours and then daily until stability was reached. Results are shown in FIGS. 3 and 4. The COMBAT Superbait crumbles in the desiccator after a few days. As can be seen in FIGS. 3 and 4, RAID containerized bait is the least dynamic, followed by Combat Superbait (containerized); the formable bait (DE Station) is the most dynamic, releasing the largest amount of water and reabsorbing the greatest amount of water. The Max Gel lost the largest amount of moisture (retained 87% of original weight; FIG. 3) and regained the least (95%, never reaching initial weight). The flowable bait of the present invention (DE gel) remains moist (95% or original weight) through desiccation and ambient regimes and the formable bait of the present invention (DE station) gains the greatest amount of moisture at high relative humidity (FIG. 3).

EXAMPLE 4

Baits were prepared as described above in Example 3. Baits were formed and initial weights taken as described above. After forming and establishing initial weights, baits were immediately placed in the RH chamber and then removed at 2,4 and 6 hours and then daily to quickly take weights at ambient conditions until stability was reached. Once stability was reached, baits were removed, weighed and then left at ambient conditions and weighed again at 2,4 and 6 hours and then daily until stability was reached. The baits were then placed back into the RH chamber where the weighing sequence was repeated. When the baits were stable, they were removed, weighed and left at ambient conditions for a final sequence of weighing at ambient conditions. This represents conditions similar to those found in a commercial kitchen or sewer. Results are shown in FIGS. 5 and 6.

Figure 5:
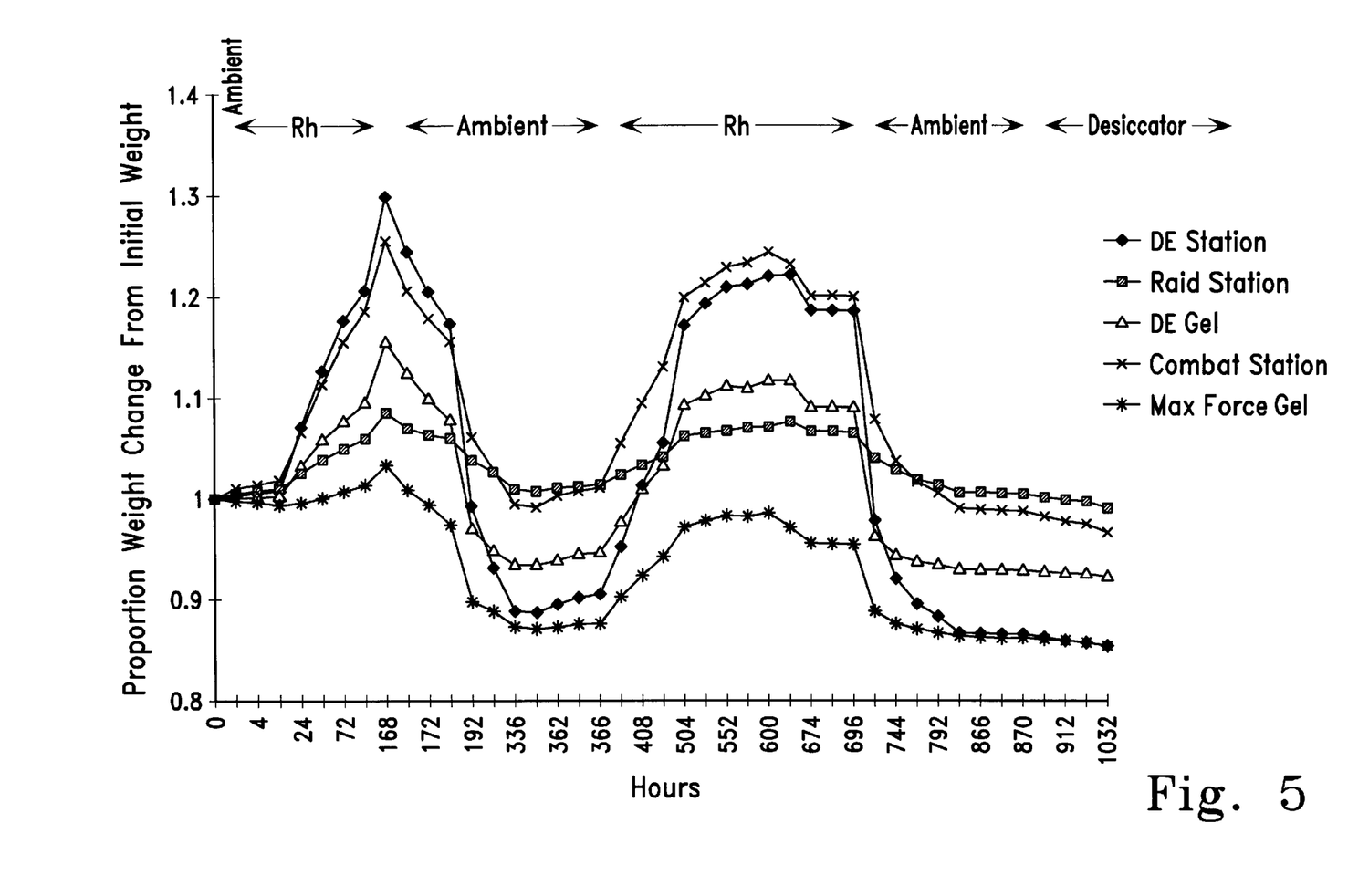
FIG. 5 is a graph comparing bait hydrodynamics of a flowable bait of the instant invention (DE Gel), a formable bait of the instant invention (DE Stat), RAID™, COMBAT™ and SIEGE™ under the following conditions: high humidity (humidity chamber, about 100% relative humidity); followed with ambient air (laboratory air, about 40–50% relative humidity), followed by high humidity (humidity chamber, about 100% humidity), followed by ambient air (laboratory air, about 40–50% relative humidity), and last dry air (desiccator, about 15% relative humidity). The weights of the baits under the various conditions are a comparison with the initial weights of the baits.
Figure 6:
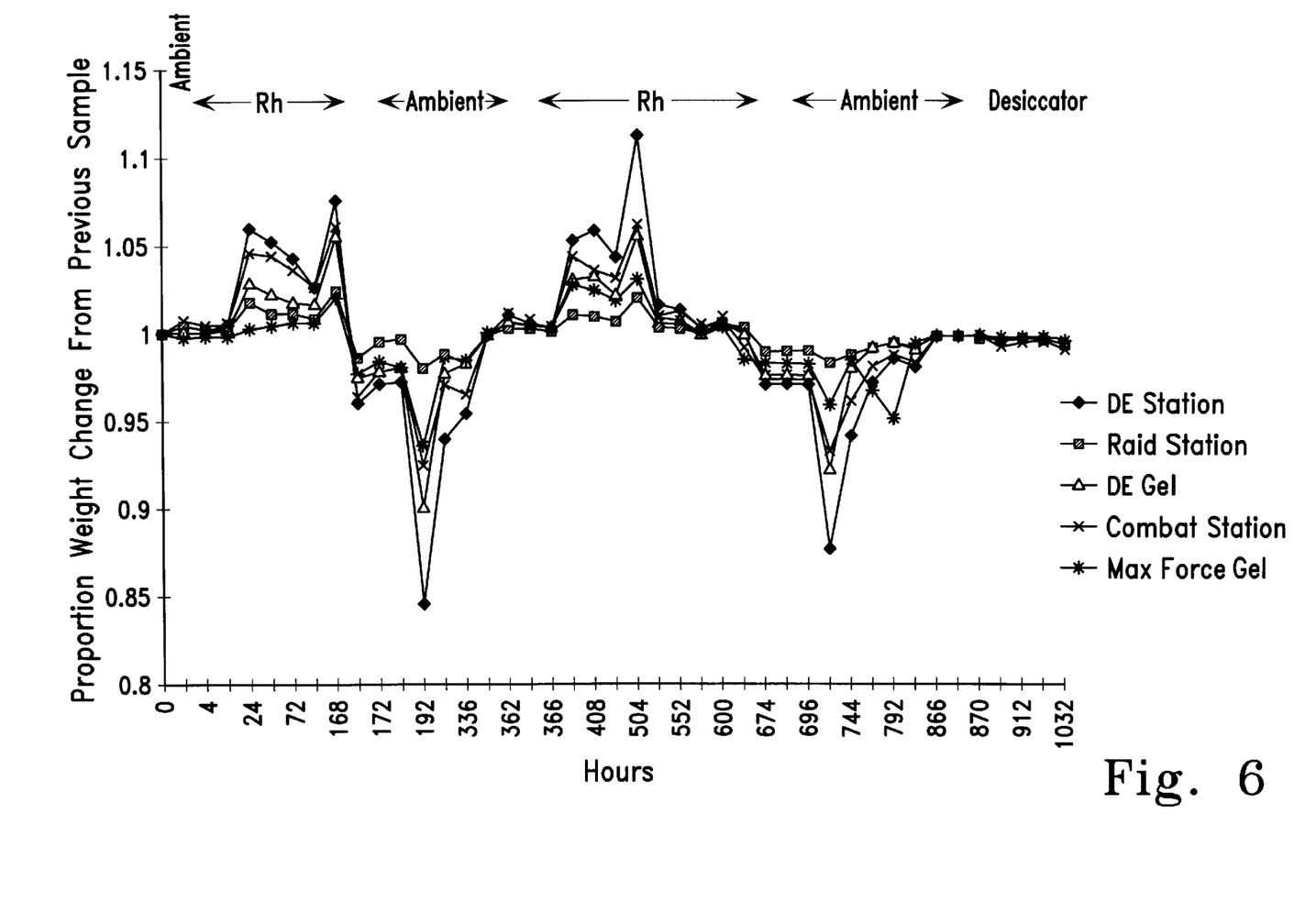
FIG. 6 is a graph comparing bait hydrodynamics of a flowable bait of the instant invention (DE Gel), a formable bait of the instant invention (DE Stat), RAID™, COMBAT™ and SIEGE™ under the following conditions: high humidity (humidity chamber, about 100% relative humidity); followed with ambient air (laboratory air, about 40–50% relative humidity), followed by high humidity (humidity chamber, about 100% humidity), followed by ambient air (laboratory air, about 40–50% relative humidity), and last dry air (desiccator, about 15% relative humidity). The weights of the baits under the various conditions are a comparison with the weight of the previous weight of that bait.

All baits absorbed moisture in the humidity chamber (RH) (FIGS. 5 and 6). The flowable bait of the present invention (DE gel) began to separate (liquid runoff) by day 4 and when removed from the chamber it did not reabsorb the liquid. The RAID Roach bait became moldy by day 8 and remained moldy even after removal from the humidity chamber. The COMBAT Superbait crumbled when removed from the humidity chamber. The most dynamic bait, exhibiting the greatest changes in moisture levels, is the formable bait (DE STAT) of the present invention. The flowable bait (DE GEL) is more dynamic over time than the COMBAT bait.

EXAMPLE 5

Trials were conducted to compare the performance of the flowable bait (DE gel) of the present invention with SIEGE Gel bait (American Cyanamid) against American cockroaches, Periplanata americana. The formulation of the baits of the present invention used in this example is: about 23.5% Grain H, about 5.2% PAYGEL 290™, about 8.3% glycerin, about 0.2% Proxel GXL, about 37.3% corn syrup containing fructose, about 0.5% chlorpyrifos, about 18.8% water, about 2,000 ppm BITREX (aq.) and about 5% peanut butter. Treatments were DE gel (3 reps), SIEGE (3 reps) and untreated controls (3 reps). Tests were conducted in large jars (battery jars) under 12 hours light and 12 hours dark at ambient temperature and humidity (indoors) with alternative food sources always available. Each replicate contained 30 cockroaches; 10 medium instar nymphs, 10 adult males and 10 adult females.

Figure 7:
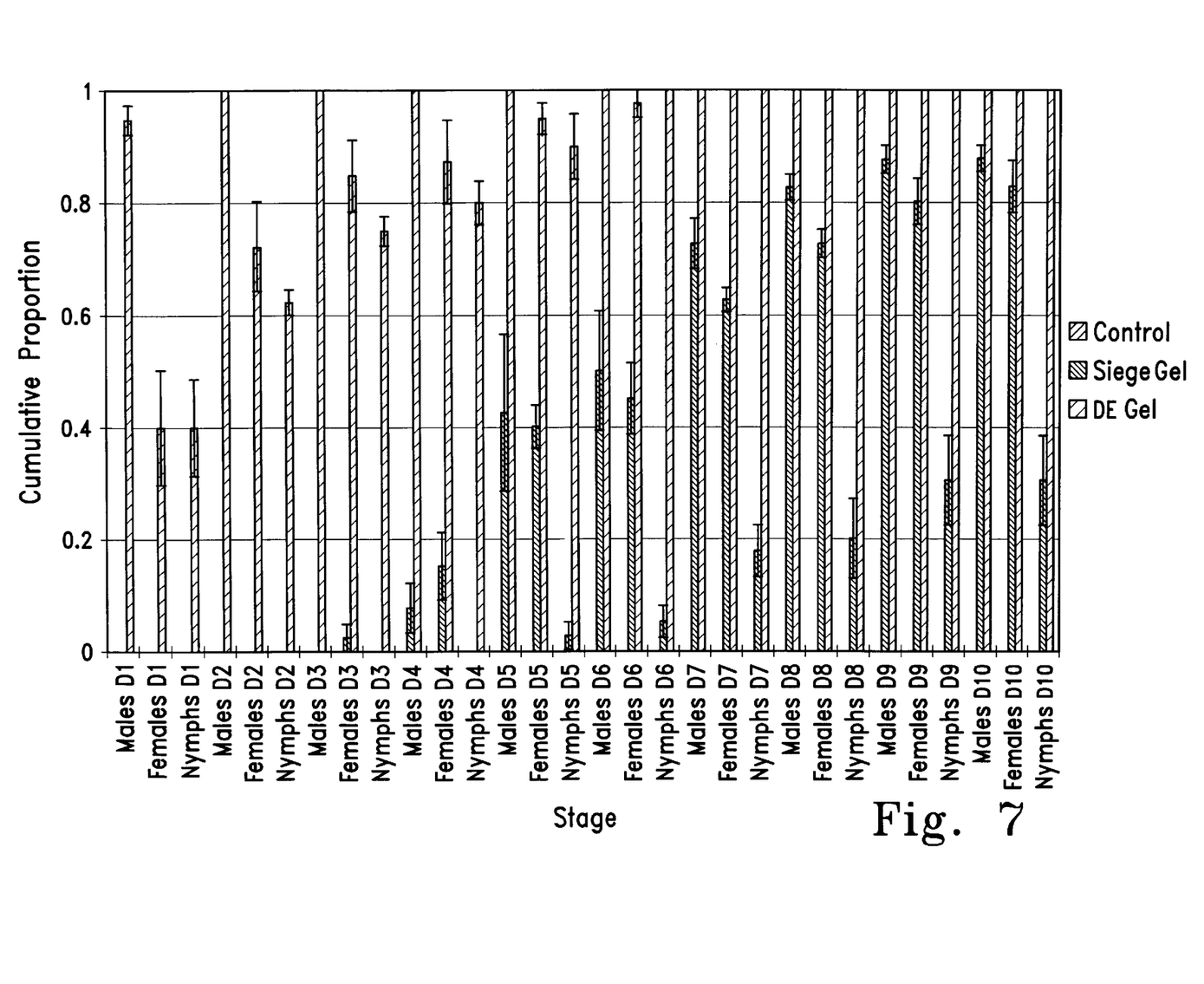
FIG. 7 is a graph comparing mean cumulative proportion mortality with SEM by stage of American cockroaches exposed to the gel bait of the present invention, DE Gel bait, or SIEGE (American Cyanamid) from about 1 day to 10 days. The DE Gel bait contained 0.5% DURSBAN™ (choropyrifos) as the toxicant and SIEGE contains 2% hydramethylnon as toxicant.
Figure 8:
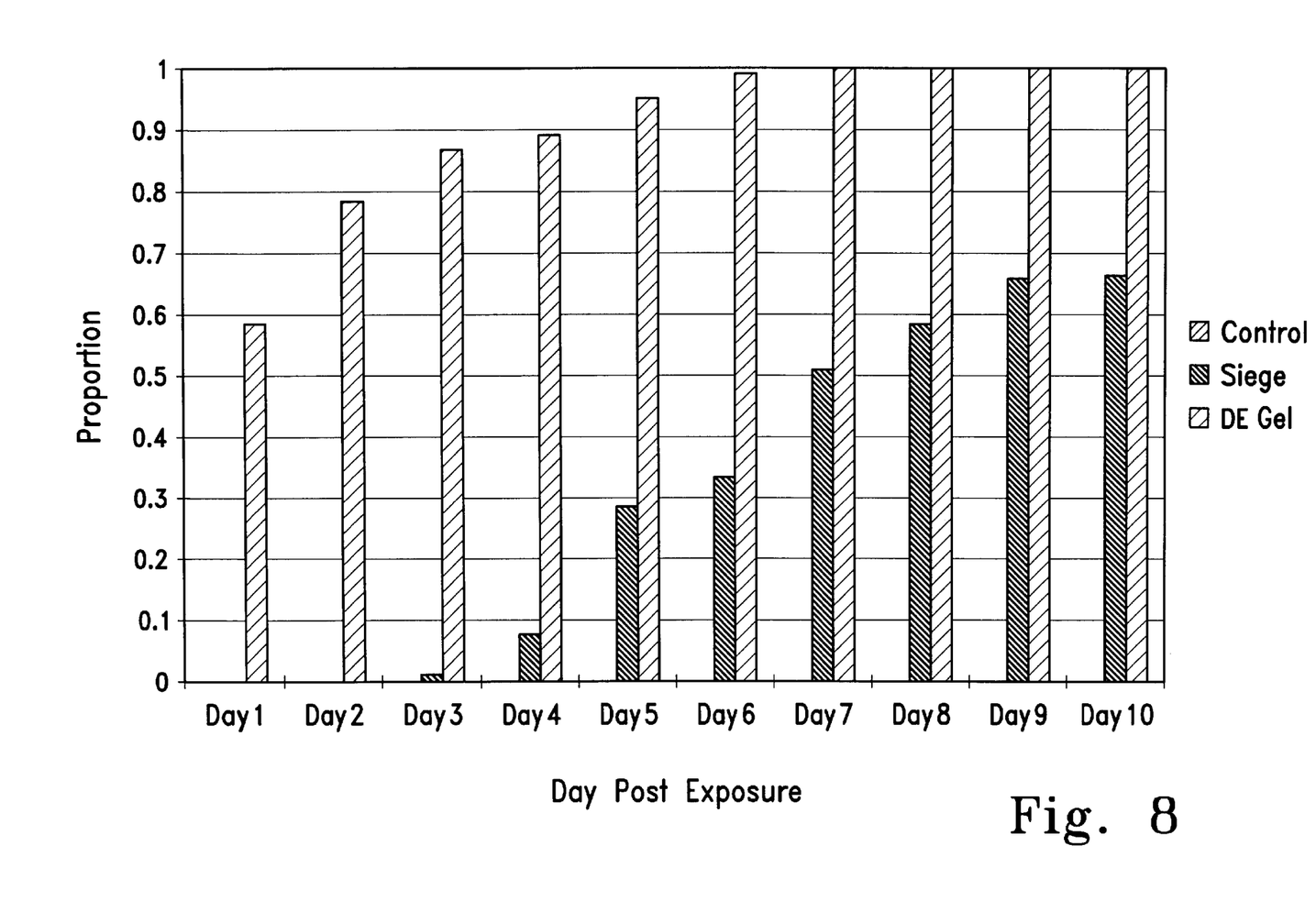
FIG. 8 is a graph showing mean proportion mortality of combined stages and replicates from the data presented in FIG. 7.
Figure 9:
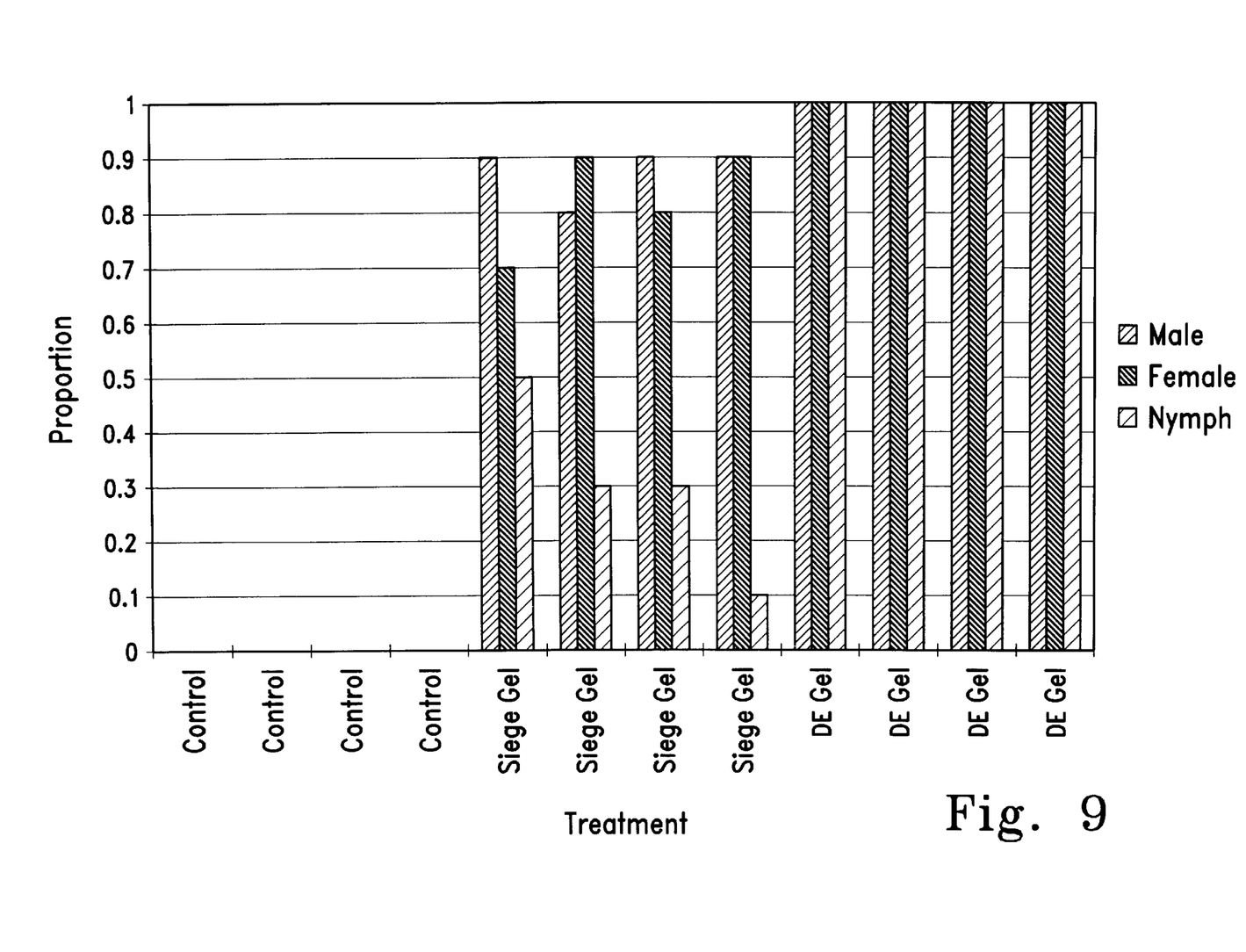
FIG. 9 is a graph showing cumulative proportion mortality by stage on Day 10 from the data presented in FIG. 7.

Roaches were chilled to facilitate sorting and counting into test jars that had the top inside 3 cm lightly coated with a mix of mineral oil and petroleum jelly (2:3 ratio, volume:volume). Cotton stoppered 5 dram water vials with water were added as well as alternative food sources consisting of PURINA laboratory RAT CHOW and FARLEY's Grape Snacks (FARLEY Candy Co., Chicago, Ill.). Cockroaches were acclimated for 2 days prior to the addition of the baits. On day 3, about 1.0 gram of each toxic bait was applied to a souffle cup. A cup was then placed in each treatment jar. Alternative food sources were replenished as needed. Each jar was checked daily, dead roaches removed and counted. The test was terminated at about 10 days post treatment. The results are shown below in FIGS. 7–9. In FIG. 7, it is shown that all males, females and nymphs are dead by day 7 in the jars containing the gel bait of the present invention (DE gel, flowable bait) whereas about 25% males, 38% females and 82% nymphs remain alive in the jars containing the SIEGE Gel bait. By day 10, the SIEGE treated replicates still contain live male, female and nymph roaches. FIG. 8 shows mean mortality of combined stages and replicates and FIG. 9 shows cumulative mortality of combined replicates by stage on day 10; both Figures are based on data shown in FIG. 7.

The foregoing detailed description is for the purpose of illustration. Such detail is solely for that purpose and those skilled in the art can make variations therein without departing from the spirit and scope of the invention.

We claim:

1. A hydrodynamic insect bait for controlling a target insect comprising an effective amount of an attractant to attract said insects, an effective amount of a mixture of high fructose corn syrup and glycerin to increase the hydrodynamic character of said bait, and a pregelatinized starch gel former; wherein said bait continuously charges and discharges moisture.

2. The bait of claim 1 wherein said attractant is selected from the group consisting of corn distiller's dried grain with solubles, peanut butter and mixtures thereof.

3. The bait of claim 1 further comprising a toxicant.

4. The bait of claim 1 further comprising a preservative.

5. The bait of claim 1 wherein the pregelatinized starch gel former is selected from the group consisting of pregelatinized wheat starch, pregelatinized cornstarch, pregelatinized tapioca, pregelatinized potato and mixtures thereof.

6. The bait of claim 1 further comprising pork gel in an amount to make a formable bait.

7. The bait of claim 5 wherein said pregelatinized starch gel former is pregelatinized wheat starch.

8. A hydrodynamic insect bait for controlling a target insect comprising an attractant to attract said insects, an effective amount of a pregelatinized starch gel to form a flowable bait, and an effective amount of high fructose corn syrup and glycerine to enhance the hydrodynamic character of said bait.

9. A hydrodynamic insect bait for controlling a target insect comprising an effective amount of an attractant to attract said insects, an effective amount of a pregelatinized starch gel to form a formable bait, an effective amount of an animal gel to form a formable bait, and an effective amount of high fructose corn syrup and glycerine to enhance the hydrodynamic character of said bait.

10. The bait of claim 9 wherein said animal gel is pork gel.

11. A method for controlling a target insect comprising applying a hydrodynamic bait to an area for control wherein said bait continuously charges and discharges moisture and comprises an effective amount of an attractant to attract said insects, an effective amount of a mixture of high fructose corn syrup an glycerin to increase the hydrodynamic character of said bait, and a pregelatinized starch gel former.

12. The method of claim 11 wherein said pregelatinized starch gel former is selected from the group consisting of pregelatinized wheat starch, pregelatinized cornstarch, pregelatinized tapioca, pregelatinized potato and mixtures thereof.

13. The method of claim 11 wherein said bait further comprises a toxicant.

14. The method of claim 11 wherein said bait further comprises a protectant.

15. The method of claim 11 wherein said bait further comprises a preservative.

16. The method of claim 11 wherein said pregelatinized starch gel is added in an amount effective to form a flowable bait.

17. The method of claim 11 wherein said pregelatinized starch gel is added in an amount effective to form a formable bait.

18. The method of claim 12 wherein said bait further comprises pork gel in an amount to make a formable bait.

19. The method of claim 11 wherein said pregelatinized starch gel former is pregelatinized wheat starch.

* * * * *

UNITED STATES PATENT AND TRADEMARK OFFICE
CERTIFICATE OF CORRECTION

PATENT NO. : 5,968,540
DATED : October 19, 1999
INVENTOR(S) : Richard J. Brenner and Kevin Burns It is certified that error appears in the above-identified patent and that said Letters Patent is hereby corrected as shown below:

On the title page, item [73] Assignee, insert the following:

Dow Agro Sciences, LLC

Indianapolis, Indiana 46268

Signed and Sealed this

Nineteenth Day of September, 2000

Attest:

Q. TODD DICKINSON

*Attesting Officer*      *Director of Patents and Trademarks*